US006395700B1

(12) United States Patent
Yamada et al.

(10) Patent No.: US 6,395,700 B1
(45) Date of Patent: May 28, 2002

(54) PROCESS FOR THE PREPARATION OF COMPOUNDS HAVING -CH$_2$-CHF-GROUPS

(75) Inventors: Toshiro Yamada; Takashi Uruma; Tatsuya Sugimoto, all of Kawasaki (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/582,325

(22) PCT Filed: Dec. 25, 1998

(86) PCT No.: PCT/JP98/05958

§ 371 (c)(1),
(2), (4) Date: Jun. 23, 2000

(87) PCT Pub. No.: WO99/33771

PCT Pub. Date: Jul. 8, 1999

(30) Foreign Application Priority Data

Dec. 26, 1997 (JP) .............................................. 9-367540

(51) Int. Cl.[7] .............................. C11D 3/24; C11D 7/30
(52) U.S. Cl. ........................ 510/412; 510/204; 570/170; 570/101; 570/123; 570/126; 570/145; 570/147; 570/149
(58) Field of Search ................................. 510/412, 204; 570/170, 101, 123, 126, 145, 147, 149

(56) References Cited

U.S. PATENT DOCUMENTS 5,045,634 A     9/1991   Fernandez et al. .......... 570/170
5,171,902 A  *  12/1992  Krespan et al. ............. 570/175

FOREIGN PATENT DOCUMENTS

EP    0 396 974         11/1990
EP      396974     *    11/1990

* cited by examiner

*Primary Examiner*—Charles Boyer
(74) *Attorney, Agent, or Firm*—Armstrong, Westerman & Hattori, LLP

(57) ABSTRACT

Compounds each having a —CH$_2$—CHF— group and a number of carbon atoms of 4 or above are prepared by hydrogenating a compound having a —CCl=CF— group and a number of carbon atoms of 4 or above in the presence of a noble metal catalyst in a liquid or gas phase. The compound having a —CCl=CF— group and a number of carbon atoms of 4 or above is preferably a C$_4$–C$_{10}$ alicyclic one, and can be prepared by reacting a compound having a —CCl=CCl— group and a number of carbon atoms of 4 or above with a fluorinating agent.

14 Claims, No Drawings

PROCESS FOR THE PREPARATION OF COMPOUNDS HAVING -CH₂-CHF-GROUPS

TECHNICAL FIELD

This invention relates to a process for preparing a compound having at least 4 carbon atoms and a —$CH_2$—CHF— group which is useful as a detergent or a solvent.

BACKGROUND ART

In processes for washing various materials in an industrial scale, a solvent composition predominantly comprised of a freon having good incombustibility, low-toxicity and good stability were heretofore widely used. However, freon destroys An ozone layer and invites global warming, and thus, regulations on suppression of the use of freon have been established and the production thereof has been absolutely prohibited all over the world.

Under these circumstances, extensive researches have been made for developing various alternatives for freon. One type of the alternatives for freon is hydrofluorocarbons having no chlorine atom which is a typical example of the ozone layer-destroying factors. It is well known that hydrofluorocarbons have no chlorine atom and are incombustible and stable. It is also known that hydrofluorocarbons exhibit satisfactory washing performance when they are used either alone or in combination with an organic solvent.

It is expected that hydrofluorocarbon compounds having a —$CH_2$—CHF— group are new fluorine-containing materials as hydrofluorocarbons having no chlorine atom. The hydrofluorocarbon compounds having a —$CH_2$—CHF— group do not destroy the ozone layer and have a short life in the air, and thus, cause the global warming only to a minimum extent. In addition, the hydrofluorocarbon compounds are capable of dissolving contaminants to an appropriate extent, do not affect plastic articles, and exhibit good stability against heat and chemicals and good incombustibility.

As for a process for preparing a chain-like hydrofluorocarbon compound having a —$CH_2$—CHF— group, only a process for preparing a hydrofluorocarbon compound having 3 carbon atoms is known. For example, a process for preparing $CF_3CH_2CHF_2$ by hydrogenating $CF_3CH=CF_2$ in the presence of a hydrogenation catalyst is described in Japanese Unexamined Patent Publication (hereinafter abbreviated to "JP-A") No. H8-2594775. A process for preparing $CF_3CH_2CHF_2$ by hydrogenating $CF_3CCl=CF_2$ in the presence of a reducing catalyst is described in Japanese Unexamined Patent Publication (hereinafter abbreviated to "JP-A") No. H8-337542. These processes have problems such that three hydrogen atoms must be introduced in the molecule in two stages and the synthesis of a raw material, $CF_3CCl=CF_2$ is troublesome and costly. Therefore, an improved process is desired.

It is known that, in a process for preparing 1,1,2,2,3,3,4,5-octafluorocyolopentane by allowing perfluorocyclopentene to react with hydrogen in the presence of a noble metal catalyst such as, for example, palladium, 1,1,2,2,3,3,4-heptafluorocyclopentane, which is an alicyclic hydrocarbon compound having a —$CH_2$—CHF— group and at least 4 carbon atoms, is produced as a side reaction product (Journal of American Chemical Society, p548, 1968). But, there is no description of separating 1,1,2,2,3,3,4-heptafluorocyclopentane from the reaction product. In fact, 1,1,2,2,3,3,4-heptafluorocyclopentane and 1,1,2,2,3,3,4,5-octafluorocyolopentane have boiling points which are very close to each other, and therefore, the former is impossible to separate from the latter by distillation.

A process for producing a compound having at least 4 carbon atoms and a —$CH_2$—CHF— group in an industrial scale has not heretofore been proposed.

DISCLOSURE OF THE INVENTION

The object of the present invention is to provide a process for producing a compound having at least 4 carbon atoms and a —$CH_2$—CHF— group with a high purity in an industrially advantageous manner.

As a result of extensive researches for achieving the object, the present inventors have found a process whereby the object hydrofluorocarbon compound can be produced at a high purity by utilizing the difference between a chlorine atom and a fluorine atom In reactivity of replacement with hydrogen.

Further, the present inventors have completed an industrially advantageous process for producing the object hydrofluorocarbon compound involving a scheme of reactions which includes a reaction for producing the starting compound need in the above-process.

In one aspect of the present invention, there is provided a process for preparing a compound having at least 4 carbon atoms and represented by the. following formula (3), characterized in that a compound having at least 4 carbon atoms and represented by the following formula (1) is hydrogenated in the presence of a noble metal catalyst in the liquid phase or the vapor phase;

$$R^1—C^1Cl=C^2F—R^2 \qquad (1)$$

wherein $R^1$ is a fluorine atom or an alkyl group having 1 to 8 carbon atoms which may be fluorinated, and $R^2$ is a hydrogen atom, a fluorine atom or an alkyl group having 1 to 8 carbon atoms which may be fluorinated, provided that at least one of $R^1$ and $R^2$ is an alkyl group having 1 to 8 carbon atoms which may be fluorinated, and that the sum of carbon atoms in $R^1$ and $R^2$ is at least two, and $R^1$ and $R^2$ may form together a divalent hydrocarbon group having 2 to 8 carbon atoms represented by the formula —$R^1$—$R^2$—, in which the entirety or a part of the hydrogen atoms in the hydrocarbon group of formula —$R^1$—$R^2$— may be fluorinated, and which forms together with $C^1$ and $C^2$ an alicyclic compound;

$$R^3—C^3H_2—C^4HF—R^4 \qquad (3)$$

wherein $R^3$ and $R^4$ are the same as $R^1$ and $R^2$ in formula (1), respectively.

In another aspect of the present invention, there is provided a process for preparing a compound having at least 4 carbon atoms and represented by the formula (3), characterized in that a compound having at least 4 carbon atoms and represented by the following formula (4):

$$R^5—C^5Cl=C^6Cl—R^6 \qquad (4)$$

wherein $R^5$ and $R^6$ are the same as $R^1$ and $R^2$ in the formula (1), respectively, is allowed to react with a fluorinating agent to give the compound having at least 4 carbon atoms and represented by the formula (1); and then the compound of formula (1) is hydrogenated in the presence of a noble metal catalyst.

BEST MODE FOR CARRYING OUT THE INVENTION

The process of the present invention is concerned with conversion of a compound having at least 4 carbon atoms and a —CCl═CF— group into a compound having at least 4 carbon atoms and a —CH₂—CHF— group by hydrogenating the former compound in the presence of a noble metal catalyst.

The compound used as the starting material in the process of the present invention is a chain-like compound or preferably an alicyclic compound, which is represented by the following formula (1). The number of carbon atoms in the main chain of the chain-like compound of formula (1) or the cyclic structure of the alicyclic compound of formula (1).

$$R^1-C^1Cl=C^2F-R^2 \quad (1)$$

wherein $R^1$ is a fluorine atom or an alkyl group having 1 to 8 carbon atoms which may be fluorinated, and $R^2$ is a hydrogen atom, a fluorine atom or an alkyl group having 1 to 8 carbon atoms. A part or the entirety of the alkyl group having 1 to 8 carbon atoms may be fluorinated. However, at least one of $R^1$ and $R^2$ is an alkyl group having 1 to 8 carbon atoms which may be fluorinated, and that the sum of carbon atoms in $R^1$ and $R^2$ is at least two. $R^1$ and $R^2$ may form together a divalent hydrocarbon group having 2 to 8 carbon atoms represented by the formula —$R^1$—$R^2$—, in which the entirety or a part of the hydrogen atoms in the hydrocarbon group of formula —$R^1$—$R^2$— may be fluorinated, and which forms together with $C^1$ and $C^2$ an alicyclic compound.

Substituents $R^1$ and $R^2$ are selected, as mentioned above, from a hydrogen atom, a fluorine atom and an unsubstituted alkyl group having 1 to 8 carbon atoms and an alkyl group having 1 to 8 carbon atoms, a part or the entirety of which is fluorinated, provided that $R^1$ is not a hydrogen atom. Of these, a fluorine atom and a perfluoroalkyl group having 1 to 8 carbon atoms are preferable.

As specific examples of the perfluoroalkyl group having 1 to 8 carbon atoms, there can be mentioned a perfluoromethyl group, a perfluoroethyl group, a perfluoro-n-propyl group. a perfluoroisopropyl group, a perfluoro-n-butyl group, a perfluoro-tert-butyl group, perfluoropentyl groups, perfluorohexyl groups, perfluoroheptyl groups and perfluorooctyl groups.

$R^1$ and $R^2$ in formula (1) may form together a divalent hydrocarbon group having 2 to 8 carbon atoms represented by the formula —$R^1$—$R^2$—, which forms together with $C^1$ and $C^2$ an alicyclic compound represented by the following formula (2).

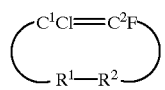

(2)

The divalent hydrocarbon group —$R^1$—$R^2$— has 2 to 8 carbon atoms, preferably 2 to 4 carbon atoms. A part or the entirety of the hydrogen atoms in the divalent hydrocarbon group may be fluorinated. Preferably the entirety of the hydrogen atoms is fluorinated.

As specific examples of a perfuoroalkylene group, i.e., a divalent hydrocarbon group of formula —$R^1$—$R^2$— having 2 to 8 carbon atoms, the entirety of which is fluorinated, there can be mentioned a perfluoroethylene group, a perfluoro-n-propylene group, a perfluoroisopropylene group, a perfluoro-n-butylene group, a perfluoro-tert-butylene group, perfluoropentylene groups, perfluorohexylene groups, perfluoroheptylene groups and perfluorooctylene groups.

As examples of the alicyclic compound of formula (2), which is formed from $C^1$ and $C^2$ and the divalent hydrocarbon group of formula —$R^1$—$R^2$— in the formula (1), there can be mentioned a cyclobutene compound, a cyclopentene compound, a cyclohexene compound, a cycloheptene compound and a cyclohexene compound. Of these, a cyclobutene compound, a cyclopentene compound and a cyclohexene compound are preferable. A cyclopentene compound is especially preferable.

The compound of formula (1) includes chain-like chlorofluoroalkene compounds and alicyclic chlorofluoroalkene compounds. As specific examples of the chain-like chlorofluoroalkene compound, there can be mentioned 1-chloroheptafluorobutene, 2-chloroheptafluorobutene, 1-chlorononafluoropentene, 2-chlorononafluoropentene, 3-chlorononafluoro-2-pentene, 1-chloroundecafluorohexene, 2-chloroundecafluorohexene and 3-chloroundecafluoro-2-hexene. As specific examples of the alicyclic chlorofluoroalkene compound, there can be mentioned 1-chloropentafluorocyclobutene, 1-chloroheptafluorocyclopentene, 1-chlorononafluorocyclohexene, 1-chloro-5-trifluoromethyloctafluorocyclohexene and 1-chloroundecafluorocycloheptene. Of these, 1-chlorononafluoropentene, 2-chlorononafluoropentene, 3-chlorononafluoro-2-pentene and 1-chloroheptafluorocyclopentene are preferable. 1-chloroheptafluorocyclopentene is most preferable.

The hydrogenation reaction will now be described.

Hydrogen used for the hydrogenation reaction is gaseous. Hydrogen is preferably used in an amount more than equimolar to the compound of formula (1). More specifically hydrogen La used preferably in an amount of at least two mols, more preferably 2 to 50 mole, per mol of the compound of formula (1).

The noble metal catalyst used is a noble metal or a noble metal compound, Preferably the noble metal catalyst is used in a form supported by a carrier. As specific examples of the noble metal, there can be mentioned palladium, rhodium, ruthenium, rhenium and platinum. Of these, palladium, rhodium and ruthenium are preferable. Palladium is most preferable. As specific examples of the noble metal compound, there can be mentioned salts such as palladium acetate, palladium sulfate and palladium nitrate, and halides such as palladium chloride.

The noble metal catalyst may be comprised of either a single metal or an alloy comprising at least two kinds of metals, i.e., a bimetal catalyst, The alloy is preferably an alloy predominantly comprised of palladium.

Kind, shape and size of the carrier used for supporting the noble metal catalyst are not particularly limited. The kinds of carrier include, for example, active carbon, silica gel, titania, zirconia and hydrogen fluoride-treated products thereof. The shape of carrier includes, for example, a powder, a sphere and a particle form such as a pellet. The particle may be either a molded particle or a pulverized product of a particulate form. Preferably the shape is a powder for the liquid phase reaction, and a particle form for the vapor phase reaction. The amount of the noble metal supported on the carrier is usually in the range of 0.05 to 20% by weight, and preferably, 0.1 to 20% by weight for a powdery carrier, and 0.1 to 10% by weight for a particulate carrier. More preferably a powdery catalyst having 0.1 to 10% by weight of a noble metal supported on a powdery carrier is used for the liquid phase reaction, and a particulate catalyst having 0.5 to 7% by weight of a noble metal supported on a particulate carrier are used.

The hydrogenation reaction is carried out In the liquid phase or the vapor phase. A solvent may be optionally used in the liquid phase reaction, and a diluent may be optionally used in the vapor phase reaction. The vapor phase reaction can be carried out, for example, by a fixed bed vapor phase reaction procedure or a fluidized bed vapor phase reaction procedure.

The solvent used in the liquid phase reaction is not particularly limited, and includes, for example, aliphatic hydrocarbons, aromatic hydrocarbons, hydrofluorocarbons, alcohols, ethers, ketones, esters and water.

The aliphatic hydrocarbons usually have 4 to 15 carbon atoms, and, as specific examples thereof, there can be mentioned n-butane, n-pentane, methylpentane, n-hexane, cyolopentane and cyclohexane.

As a specific example of the aromatic hydrocarbons, there can be mentioned trifluoromethylbenzene.

As specific examples of the hydrofluorocarbons, there can be mentioned pentafluoroethane, pentafluoropropane, hexafluorobutane and decafluoropentane.

The alcohols usually have 1 to 10 carbon atoms, preferably 1 to 6 carbon atoms, and, as specific examples of the alcohols, there can be mentioned methanol, ethanol, propanol, butanol and cyclopentanol.

The ethers usually have 4 to 10 carbon atoms, preferably 4 to 6 carbon atoms, and, as specific examples of the ethers, there can be mentioned diethyl ether, diisopropyl ether and ethylene glycol dimethyl ether.

The ketones usually have 3 to 10 carbon atoms, preferably 3 to 8 carbon atoms, and, as specific examples of the ketones, there can be mentioned acetone, methyl ethyl ketone, methyl isopropyl ketone, methyl butyl ketone and cyclopentanone.

The esters usually have 4 to 10 carbon atoms, preferably 3 to 8 carbon atoms, and, as specific examples of the esters, there can be mentioned ethyl acetate, butyl acetate, propyl acetate, methyl propionate, methyl butyrate and methyl valerate.

These solvents may be used either alone or as a combination of at least two thereof. The amount of the solvent is not particularly limited, but it is usually in the range of 0 to 80 parts by weight, preferably 0 to 50 parts by weight, based on 100 parts by weight of the compound having a —CCl=CF— group.

The diluent used in the vapor phase reaction is inert to the hydrogenation reaction, and includes nitrogen gas, rare gas, hydrocarbon gas and hydrofluorocarbon gas. As specific examples of the diluent, there can be mentioned rare gas such as argon gas and helium gas; hydrocarbon gas such as methane gas, ethane gas, propane gas and butane gas; and hydrofluorocarbon gas such as pentafluoroethane, pentafluoropropane, hexafluorobutane and decafluoropentane.

These diluents may be used either alone or as a combination of at least two there of, The amount of the diluent is not particularly limited, but it is usually in the range of 0 to 500 parts by weight, preferably 0 to 200 parts by weight, based on 100 parts by weight of the compound having a —CCl=CF— group.

The pressure in the hydrogenation reaction system is usually in the range of about normal pressure to about 50 kgf/cm$^2$, and preferably normal pressure to 20 kgf/cm$^2$. The reaction temperature is usually in the range of about normal temperature to about 350° C., and preferably about normal temperature to about 200° C., If desired, the reaction system can be stirred or shaken.

The hydrogenation reaction of the present invention can be carried out by a batchwise manner or a continuous manner wherein a raw material is continuously fed into a reactor and a reaction product is continuously withdrawn from the reactor.

The reaction vessel used is a pressure vessel for a batchwise reaction manner and one or more reactors connected in series, for example, cascade reactors, for a continuous reaction manner. The material of the reaction vessel is preferably, for example, stainless steel. The reaction vessel made of stainless steel is preferably subjected to conditioning by a treatment with nitric acid prior to the use thereof.

In the hydrogenation reaction, acidic ingredients such as hydrogen chloride gas are produced as by-products. It is preferable to remove the acidic ingredients by absorption or neutralization during the reaction. The removal can be carried out by incorporating an additive into the reaction system. The additive includes, for example, hydroxides, oxides, weak acid salts and organic acid salts of an alkali metal or an alkaline earth metal. As specific examples of the additive, there can be mentioned soda lime, quick lime, alkali metal carbonate and alkali metal acetate. These additives may be used either alone or as a combination of at least two thereof. The additive is usually used In an amount of at least equivalent to the compound of formula (1).

After completion of the hydrogenation reaction, if desired, an additive Is incorporated in the reaction mixture to remove acidic ingredients by adsorption or neutralization, thereafter the objective compound is separated by a conventional purification procedure such as distillation.

The objective compound produced by the process of the present invention is a compound having at least 4 carbon atoms and represented by the following formula (3), which is a chain-like compound or an alicyclic compound, An alicyclic compound is preferable as the compound of formula (3). The number of carbon atoms contained in the main chain of the chain-like compound or in the cyclic structure of the alicyclic compound is usually in the range of 4 to 10, preferably 4 to 6 and most preferably 5

$$R^3—C^3H_2—C^4HF—R^4 \qquad (3)$$

wherein R$^3$ and R$^4$ are the same as R$^1$ and R$^2$ in the above-mentioned formula (1), respectively. As being the same as in the formula (1), one of R$^3$ and R$^4$ is an alkyl group having 1 to 8 carbon atoms which may be fluorinated; the sum of carbon atoms in R$^3$ and R$^4$ is at least two; and R$^3$ and R$^4$ may form together a divalent hydrocarbon group having 2 to 8 carbon atoms represented by the formula —R$^3$—R$^4$—, which forms together with C$^3$ and C$^4$ an alicyclic compound.

As specific examples of the perfluoroalkyl group having 1 to 8 carbon atoms, which is a preferable example of R$^3$ and R$_4$, there can be mentioned those which are recited as for R$^1$ and R$^2$ in formula (1). As specific examples of the perfluoroalkylene group having 2 to 8 carbon atoms, represented by the formula —R$^3$—R$^4$—, there can be mentioned those which are recited as for —R$^1$—R$^2$—.

The compound of formula (3) having at least 4 carbon atoms includes chain-like compounds and alicyclic compounds. As specific examples of the chain-like compound, there can be mentioned 1,1,1,2,4,4,4-heptafluoro-n-butane, 1,1,1,2,2,3,5,5,5-nonafluoro-n-pentene, 1,1,1,2,2,4,5,5,5-nonafluoro-n-pentene, 1,1,1,2,2,3,3,4,6,6,6-undecafluoro-n-hexane, 1,1,1,2,2,3,3,5,6,6,6-undecafluoro-n-hexane and 1,1,1,2,2,4,5,5,6,6,6-undecafluoro-n-hexane. As specific examples of the alicyclic compound, there can be mentioned 1,1,2,2,3-pentafluorocyclobutane, 1,1,2,2,3,3,4-heptafluorocyclopentane and 1,1,2,2,3,3,4,4,5-nonafluorocyclohexane. Of these, 1,1,1,2,2,3,5,5,5-nonafluoro-n-pentene and 1,1,2,2,3,3,4-heptafluorocyclopentane are preferable. 1,1,2,2,3,3,4-heptafluorocyclopentane is most preferable.

The process for preparing the compound having at least 4 carbon atoms, represented by the formula (1), which is used as a starting raw material for the hydrogenation reaction, is not particularly limited, but, preferably the compound of formula (1) is prepared by allowing a compound having at least 4 carbon atoms, represented by the following formula (4), to react with a fluorinating agent. In this reaction, one of the two chlorine atoms in the group —$C^5Cl$=$C^5Cl$— of the compound of formula (4) is substituted by a fluorine atom.

The compound represented by the following formula (4), used in the present invention, is a chain-like compound or an alicyclic compound. An alicyclic compound is preferable. The number of carbon atoms in the main chain or cyclic structure of the compound of formula (4) are usually in the range of 4 to 10, preferably 4 to 6 and most preferably 5.

  (4)

In the formula (4), $R^5$ and $R^6$ are the same as $R^1$ and $R^2$, respectively, in the formula (1). As being the same as $R^1$ and $R^2$ in the formula (1). one of $R^5$ and $R^6$ is an alkyl group having 1 to 8 carbon atoms which may be fluorinated; the sum of carbon atoms in $R^5$ and $R^6$ is at least two, and $R^5$ and $R^6$ may form together a divalent hydrocarbon group having 2 to 8 carbon atoms represented by the formula —$R^5$—$R^6$—, which forms together with $C^5$ and $C^6$ an alicyclic compound.

As specific examples of the perfluoroalkyl group having 1 to 8 carbon atoms, which is a preferable example of $R^5$ and $R^6$, there can be mentioned those which are recited as for $R^1$ and $R^2$ in formula (1). As specific examples of the perfluoroalkylene group having 2 to 8 carbon atoms, represented by the formula —$R^5$—$R^6$—, there can be mentioned those which are recited as for —$R^1$—$R^2$— in the formula (1).

As specific examples of the chain-like compound of formula (4), there can be mentioned 1,2-dichlorohexafluoro-1-butene, 2,3-dichlorohexafluoro2-butene, 1,2-dichlorooctafluoro-1-pentene, 2,3-dichlorooctafluoro-2-pentene and 1,2-dichlorodecafluoro-1-hexene. As specific examples of the alicyclic compound of formula (4), there can be mentioned 1,2-dichloroteterafluorocyclobutene-1,1, 2-dichlorohexafluorocyclopentene-1 and 1,2-dichlorooctafluoracyclohexene-1, Of these, 1,2-dichlorooctafluoro-1-pentene, 2,3-dlchlorooctafluoro-2-pentene and 1,2-dichlorohexafluorocyclopentene-1 are preferable. 1,2-dichlorohexafluorocyclopentene-1 is most preferable.

The fluorinating agent used is not particularly limited, provided that it is capable of releasing a fluorine ion. As examples of the fluorinating agent, there can be mentioned metal fluorides, aqueous or anhydrous hydrofluoric acid, associated products of hydrofluoric acid with an amine or a quaternary ammonium salt, and an associated product of hydrofluoric acid with a polar solvent. Of these, metal fluorides are preferable.

The metal fluorides include, for example, fluorides of an alkali metal, an alkaline earth metal and a transition metal. Of these, alkali metal fluorides are preferable. As specific examples of the alkali metal fluorides, sodium fluoride, potassium fluoride and lithium fluoride. Potassium fluoride is most preferable. These fluorinating agents may be used either alone or as a combination of at least two thereof.

The amount of the fluorinating agent is at least 0.5 mol per mol of the compound having at least 4 carbon atoms of formula (4). However, in order to prevent substitution of both of the two chlorine atoms in the —ClC=CCl— group, the amount of the fluorinating agent is preferably not larger than 2 mols, more preferably in the range of 0.5 to 1.2 mole, per mol of the compound of formula (4).

The fluorinating reaction may be carried out either in the liquid phase or the vapor phase, When an alkali metal hydride is used, the fluorinating reaction Is usually carried out in the liquid phase under normal pressure.

When the fluorinating reaction is carried out in the liquid phase, a solvent can be used, As the solvent, an aprotic polar solvent is usually used. As specific examples of the aprotic polar solvent, there can be mentioned N-methylpyrrolidone, N,N-dimethylformamide, N,N-dimethylacetamide and N,N'-dimethylimidazolidinone. Of these, N-methylpyrrolidone and N,N-dimethylformamide are preferable. These solvents may be used either alone or as a mixture of at least two thereof. If desired, these aprotic polar solvents may be used in combination with compatible aromatic hydrocarbon solvents such as benzene, toluene, xylene and mesitylene.

The amount of the Solvent is not particularly limited, but is usually in the range of 0 to 1,000 parts by weight based on 100 parts by weight of the compound of formula (4).

The reaction temperature in the liquid phase reaction is appropriately chosen from the range of 20° C. to 200° C., preferably 50° C. to 150° C. and more preferably 80° C. to 130° C.

When the reaction is carried out in the liquid phase, the reaction is preferably effected In a solvent having a metal fluoride dispersed therein, by using a reaction vessel equipped with a distillation column. In this liquid phase reaction, it is preferable that only the objective compound is concentrated and separated at a high purity from the top part of the distillation column, and simultaneously, the raw material and intermediate reaction products are returned under reflux to the reaction vessel without discharge therefrom.

When the fluorinating reaction is carried out in the vapor phase reaction, a diluent can be used. As specific examples of the diluent, there can be mentioned solvents which are recited as examples of the solvent used in the liquid phase reaction.

The reaction temperature in the vapor phase reaction is appropriately chosen from the range of 100° C. to 500° C.

The fluorinating reaction can be carried out either in a batchwise manner or a continuous manner wherein the raw material is continuously fed into a reaction vessel and the reaction product is continuously withdrawn from the reaction vessel.

When alkali metal fluorides such as potassium fluoride are used as a fluorinating agent in the fluorinating reaction, alkali metal chlorides such as potassium chloride are produced as by-products. These by-products are removed by filtration or washing with water, after completion of the reaction.

In the case of the vapor phase reaction, unreacted fluorinating agent is preferably removed by absorption or neutralization. When unreacted fluorinating agent is removed. an additive can be added in the reaction mixture, if desired. The additive used includes hydroxides, oxides, weak acid salts and organic acid salts of alkali metals and alkaline earthmetals As specific examples of the additive, there can be mentioned soda lime, quicklime, alkali carbonate and alkali acetate. These additives may be added either alone or de a combination of at least two thereof.

The amount of the additive used is usually at least one equivalent to the compound of formula (4).

After completion of the reaction, the reaction product is purified by an ordinary procedure such as distillation, or dried as it is, to give the compound of formula (1).

The invention will now be specifically described by the following examples. In the examples, % is by weight.

EXAMPLE 1

Fluorination of Dichloroalkene

A glass flask equipped with a distillation column at the upper part thereof was charged with 1,2-dichlorohexafluorocyclopentene (50.10 g, 0.205 mol), potassium fluoride (13.05 g, 0.225 mol) and N,N-dimethylformamide (50 ml), and the content was heated to 120° C. with stirring. When 0.3 hour elapsed from the commencement of heating, production of a distillate was begun. After completion of the distillation, the pressure within the flask was reduced and the residue was collected in a cooling trap. The distillate and the collected residue were combined together, and then neutralized and washed with an aqueous sodium bicarbonate solution. The analysis of the thus-obtained product showed that the objective compound 1-chloroheptafluorocyclopentene was obtained in a yield of 79.1%, Vapor Phase Hydrogenation of Chlorofluoroalkene A pressure reaction vessel was charged with the thus-obtained 1-chloroheptafluorocyolopentene (15 g, 65.6 m-mols), a 5%-palladium carbon catalyst (5% by weight), sodium acetate (10.9 g) and water (25.0 ml). and the content was stirred under a hydrogen pressure of 10 kgf/cm$^2$. After 24 hours elapsed, the reaction liquid was filtered to remove the catalyst, and the organic phase was separated and washed with water. Unreacted materials were removed from the thus-obtained product. Analysis of the product showed that the objective compound 1,1,2,2,3,3,4-heptafluorocyclopentane and a by-product 1,1,2,2,3,3-heptafluorocyclopentane were obtained in a proportion of 50% and 40%, respectively. The product was fractionated to give 1,1,2,2,3,3,4-heptafluorocyclopentane at a purity of 98%. 1,1,2,2,3,3,4-heptafluorocyclopentane had a boiling point of 80° C./760 mmHg, 1,1,2,2,3,3-heptafluorocyclopentane had a boiling point of 87° C./760 mmHg.

EXAMPLE 2

Liquid Phase Hydrogenation of Chlorofluoroalkene

By the same procedures as described in Example 1, 1-chloroheptafluorocyclopentene was prepared and then hydrogenated wherein sodium acetate and water were not used in the hydrogenation and the hydrogenation reaction time was varied to 30 hours. All other conditions remained the same. Unreacted materials were removed from the thus-obtained product. Analysis of the product showed that the objective compound 1,1,2,2,3,3,4-heptafluorocyclopentane and a side reaction product 1,1,2,2,3,3-heptafluorocyclopentane were obtained in a proportion of 70% and 2%, respectively.

EXAMPLE 3

Fluorination of Dichloroalkene

A 500 ml glass flask equipped with a distillation column at the upper part thereof was charged with 1,2-dichlorohexafluorocyclopentene (254 g, 1.04 mole), potassium fluoride (66 g, 1.14 mols) and N,N-dilmethylformamide (150 ml), and the content was heated to 110° C. with stirring. When 0.5 hour elapsed from the commencement of heating, production of a distillate was begun. The reaction product was begun to be drawn from the top of the distillation column at a reflux ratio of 10:1 and collected in a receptacle which was immersed in an ice-water and dry ice-acetone bath. While the drawing of the reaction product was continued, the heating temperature was gradually elevated, and, when the temperature of the top of the distillation column reached the boiling point of N,N-dimethylformamide, the heating was stopped. Thus, 225 g of a crude product was obtained. Analysis of the crude product by gas chromatography revealed that the contents of 1-chloro-2,3,3,4,4,5,5-heptafluorocyclopentane and 1,2,3,3,4,4,5,5-octafluorocyclopentene were 98.8% and 1.2%, respectively.

Then the crude product was distilled by a fractionating column with a theoretical plate number of 8 to collect a fraction having a boiling point of 56° C./760 mmHg. Thus 197 g (yield; 89%) of 1-chloro-2,3,3,4,4,5,5-heptafluorocyclopentene with a purity of 99.9% was obtained.

Vapor Phase Hydrogenation of Chlorofluoroalkene

The obtained 1-chloro-2,3,3,4,4,5,5-heptafluorocyclopentene was hydrogenated in the liquid phase by the same procedures as mentioned in Example 1. The results were similar to those obtained in Example 1.

EXAMPLE 4

Fluorination of Dichloroalkene

A 300 ml glass flask equipped with a distillation column at the upper part thereof was charged with 1,2-dichlorohexafluorocyclopentene (104 g, 0.42 mol), potassium fluoride (27 g, 0.47 mol), N,N-dimethylformamide (50 ml) and toluene (50 ml), and the content was heated to 95° C. with stirring. When 2.5 hours elapsed from the commencement of heating, a distillate was begun to appear. The reaction product was begun to be drawn from the top of the distillation column at a reflux ratio of 10:1 and collected in a receptacle which was immersed in an ice-water and dry ice-acetone bath. While the drawing of the reaction product was continued, the heating temperature was gradually elevated, and, when the temperature of the top of the distillation column reached the boiling point of toluene, the heating was stopped. Thus, 85 g of a crude product was obtained. Analysis of the crude product by gas chromatography revealed that the contents of 1-chloro-2,3,3,4,4,5,5-heptafluorocyclopentene, 1,2,3,3,4,4,5,5-octafluorocyclopentene and 1,2-dichlorohexafluorocyclopentene were 98.8%, 0.2% and 1.0%, respectively.

Vapor Phase Hydrogenation of Chlorofluoroalkene

The obtained 1-chloro-2,3,3,4,4,5,5-heptafluorocyclopentene was hydrogenated in the liquid phase by the same procedures as mentioned in Example 2. The results were similar to those obtained in Example 2.

EXAMPLE 5

Fluorination of Chlorofluoroalkene

An SUS 316 reaction tube having a diameter of ½ inch and a length of 15 cm and equipped with an external electric oven was packed with 5 ml of a palladium catalyst (supplied by Nikki Kagaku K.K,.) comprising 0.5% by weight of palladium supported on alumina spheres. The catalyst-packed reaction tube was heated to 150° C. The heated reaction tube was pre-treated with hydrogen by flowing hydrogen gas through the tube at a rate of 200 ml/min for 8 hours. Thereafter 1-chloro-2,3,3,4,4,5,5-heptafluoro-cyclopentene was supplied at a rate of 0.1 ml/min to a vaporizer maintained at 100° C., and the hydrogenation was carried out for 30 hours. The thus-produced gaseous mixture was washed with water, and dried with calcium chloride, and then collected in a glass trap cooled to −78° C. Analysis of the collected product by gas chromatography revealed that the conversion of the raw material was 99%, and the contents of 1,1,2,2,3,3,4-heptafluorocyclopentene, 1,3,3,4,4, 5,5-heptafluoro-cyclopentene and 1,1,2,2,3,3-hexafluorocyclopentane were 90%, 8.5% and 0.5%, respectively.

EXAMPLE 6

Fluorination of Chlorofluoroalkene

An SUS 316 reaction tube having a diameter of ½ inch and a length of 15 cm and equipped with an external electric oven was packed with 5 ml of a palladium catalyst (supplied by Nikki Kagaku K.K.) comprising 0.5% by weight of palladium supported on active carbon, The catalyst-packed reaction tube was heated to 150° C. The heated reaction tube was pre-treated with hydrogen by flowing hydrogen gas through the tube at a rate of 200 ml/min for a hours. Thereafter 1-chloro-2,3,3,4,4,5,5-heptafluoro-cyclopentene was supplied at a rate of 0.1 ml/min to a vaporizer maintained at 100° C., and the hydrogenation was carried out for 20 hours. The thus-produced gaseous mixture was washed with water, and dried with calcium chloride, and then collected in a glass trap cooled to −78° C. Analysis of the collected product by gas chromatography revealed that the conversion of; the raw material was 99%, and the contents of 1,1,2,2,3,3,4-heptafluorocyclopentene, 1,3,3,4,4,5,5-heptafluorocyclopentene and 1,1,2,2,3,3-hexafluorocyclopentane were 89%, 4% and 6%, respectively.

EXAMPLE 7

Preparation of Catalyst

An SUS 316 reaction tube having a diameter of 2.54 cm and a length of 40 cm was packed with 50 ml of a palladium catalyst (supplied by Nikki Kagaku K.K.; average particle diameter 3 mm) comprising 0.5% by weight of palladium supported on alumina spheres. Nitrogen gas was allowed to flow at a rate of 100 ml/min through the reaction tube while it was heated to 250° C. The heated reaction tube was dried for two hours, and then the temperature was further elevated to 300° C., and hydrogen fluoride gas was supplied to the tube at a rate of 400 ml/min, When it was observed that the generation of water ceased, the supply of hydrogen fluoride was stopped. Then nitrogen gas was allowed to flow at a rate of 50 ml/min to remove the surplus hydrogen fluoride.

Vapor Phase Fluorination of Chlorofluoroalkene

An SUS 316 reaction tube having a diameter of ½ inch and a length of 15 cm was packed with 5 ml of the catalyst prepared above in the same manner as mentioned in Example 5. The catalyst-packed reaction tube was pre-treated with hydrogen by flowing hydrogen gas through the tube at a rate of 200 ml/min for 10 hours. Thereafter 1-chloro-2,3,3,4,4,5,5-heptafluorocyclopentene was supplied at a rate of 0.1 ml/min to a vaporizer maintained at 100° C. and the hydrogenation was carried out for 20 hours. The thus-produced gaseous mixture was washed with water, and dried with calcium chloride, and then collected in a glass trap cooled to −78° C. Analysis of the collected product by gas chromatography revealed that the conversion of the raw material was 99%, and the contents of 1,1,2,2,3,3,4-heptafluorocyclopentene, 1,3,3,4,4,5,5-heptafluorocyclopentene and 1,1,2,2,3,3-hexafluorocyclopentane were 92%, 6.3%, and 0.7%, respectively.

Industrial Application

According to the present invention, the compound having at least 4 carbon atoms of formula (3) can be produced industrially advantageously at a high purity from the compound having at least 4 carbon atoms from of formula (1).

The produced compound having at least 4 carbon atoms of formula (3) does not destroy of the ozone-layer, and therefore, has a wide use including a detergent and a solvent as an alternative for freon.

What is claimed is:

1. A process for preparing a compound having at least 4 carbon atoms and represented by the following formula (3), characterized in that a compound having at least 4 carbon atoms and represented by the following formula (1) is hydrogenated in the presence of a noble metal catalyst in the liquid phase or the vapor phase:

$$R^1—C^1Cl=C^2F—R^2 \quad (1)$$

wherein $C^1$ and $C^2$ designate two carbon atoms of the compound; and wherein $R^1$ is an alkyl group having 1 to 8 carbon atoms which may be fluorinated, and $R^2$ is an alkyl group having 1 to 8 carbon atoms which may be fluorinated, and $R^1$ and $R^2$ may form together a divalent hydrocarbon group having 2 to 8 carbon atoms represented by the formula —$R^1$—$R^2$—, in which the entirety or a part of the hydrogen atoms in the hydrocarbon group of formula —$R^1$—$R^2$— may be fluorinated, and which forms together with $C^1$ and $C^2$ an alicyclic compound;

$$R^1—C^1H_2—C^2HF—R^2 \quad (3).$$

2. The preparation process according to claim 1, wherein the compound a having at least 4 carbon atoms, represented by formula (1), is an alicyclic compound having 4 to 10 carbon atoms in the cyclic structure.

3. The preparation process according to claim 1, wherein the compound having at least 4 carbon atoms and represented by formula (1) is 1-chloro-2,3,3,4,4,5,5-heptafluorocyclopentene.

4. The preparation process according to claim 1, wherein the noble metal catalyst is used in a form supported on a carrier; the amount of the catalyst supported is in the range of 0.05 to 20% by weight based on the carrier.

5. The preparation process according to claim 1, wherein the noble metal catalyst comprises at least one metal selected from palladium, rhodium and ruthenium.

6. The preparation process according to claim 1, wherein at least two mols of hydrogen, per mol of the compound of formula (1), is used for the hydrogenation.

7. The preparation process according to claim 1, wherein the hydrogenation is carried out at a reaction temperature in the range of room temperature to 350° C. and a reaction pressure in the range of normal pressure to 50 kgf/cm$^2$.

8. The preparation process according to claim 1, wherein the hydrogenation is carried out in the vapor phase.

9. The preparation process according to claim 1, wherein the compound of the formula (1) is prepared by allowing a compound having at least 4 carbon atoms and represented by the following formula (4):

$$R^1C^1Cl=C^2Cl—R^2 \quad (4)$$

wherein $C^1$ and $C^2$ designate two carbon atoms of the compound;

and $R^1$ and $R^2$ are the same as $R^1$ and $R^2$ in the formula (1), respectively, to react with a fluorinating agent.

10. The preparation process according to claim 9, wherein the reaction of the compound of formula (4) having at least 4 carbon atoms with the fluorinating agent to give the compound of formula (1) having at least 4 carbon atoms is carried out in a reaction vessel equipped with a distillation column while a reaction product is continuously withdrawn from the reaction system.

11. The preparation process according to claim 9, wherein the fluorinating agent is used in an amount of 0.5 to 2 mols per mol of the compound of formula (4) having at least 4 carbon atoms.

12. The preparation process according to claim 9, wherein the fluorinating agent is potassium fluoride.

13. The preparation process according to claim 9, wherein the fluorinating reaction is carried out in an aprotic polar solvent or a mixed solvent comprising an aprotic polar solvent and an aromatic hydrocarbon.

14. The preparation process according to claim 13, wherein the aprotic polar solvents are N,N-dimethylformamide and the aromatic hydrocarbon is at least one selected from benzene, toluene and xylene.

* * * * *